United States Patent [19]

Hackett

[11] 4,046,016

[45] Sept. 6, 1977

[54] MOLTEN STEEL SAMPLERS

[76] Inventor: Robert J. Hackett, Cross Road, Brookfield Center, Conn. 06805

[21] Appl. No.: 754,561

[22] Filed: Dec. 27, 1976

Related U.S. Application Data

[63] Continuation-in-part of Ser. No. 644,082, Dec. 24, 1975, abandoned.

[51] Int. Cl.² .............................................. G01N 1/12
[52] U.S. Cl. .............................................. 73/425.4 R
[58] Field of Search ..................... 73/425.4 R, DIG. 9, 73/354

[56] References Cited

U.S. PATENT DOCUMENTS

| | | | |
|---|---|---|---|
| 3,415,124 | 12/1968 | Collins | 73/425.4 |
| 3,452,602 | 7/1969 | Hackett | 73/DIG. 9 |
| 3,913,404 | 10/1975 | Boron | 73/425.4 R |

FOREIGN PATENT DOCUMENTS

| | | | |
|---|---|---|---|
| 2,064,228 | 12/1970 | Germany | 73/DIG. 9 |

Primary Examiner—S. Clement Swisher
Attorney, Agent, or Firm—Mattern, Ware, Davis & Stoltz

[57] ABSTRACT

Immersion samplers for taking disc samples and pin samples, from heats of molten steel, alloys or other metal in basic oxygen furnaces, electric furnaces and open-hearth furnaces, are provided with slotted riser vent tubes serving to retard the escape of atmospheric air displaced by the inflowing molten metal entering the deeply immersed sampler while maintaining ample cross-sectional venting area despite accumulated droplets of spattered molten metal solidifying and blocking the vents. For use with melts of unkilled steel, apertured de-oxidizing retort portals are provided at the entrance end of the samplers with protective slag covers and vent apertures, creating a substantial de-oxidizing zone for the melt entering the sampler while releasing entrapped air during the sampler's immersion, and also allowing draining of the melt from the portal upon withdrawal of the immersed sampler from the furnace.

15 Claims, 24 Drawing Figures

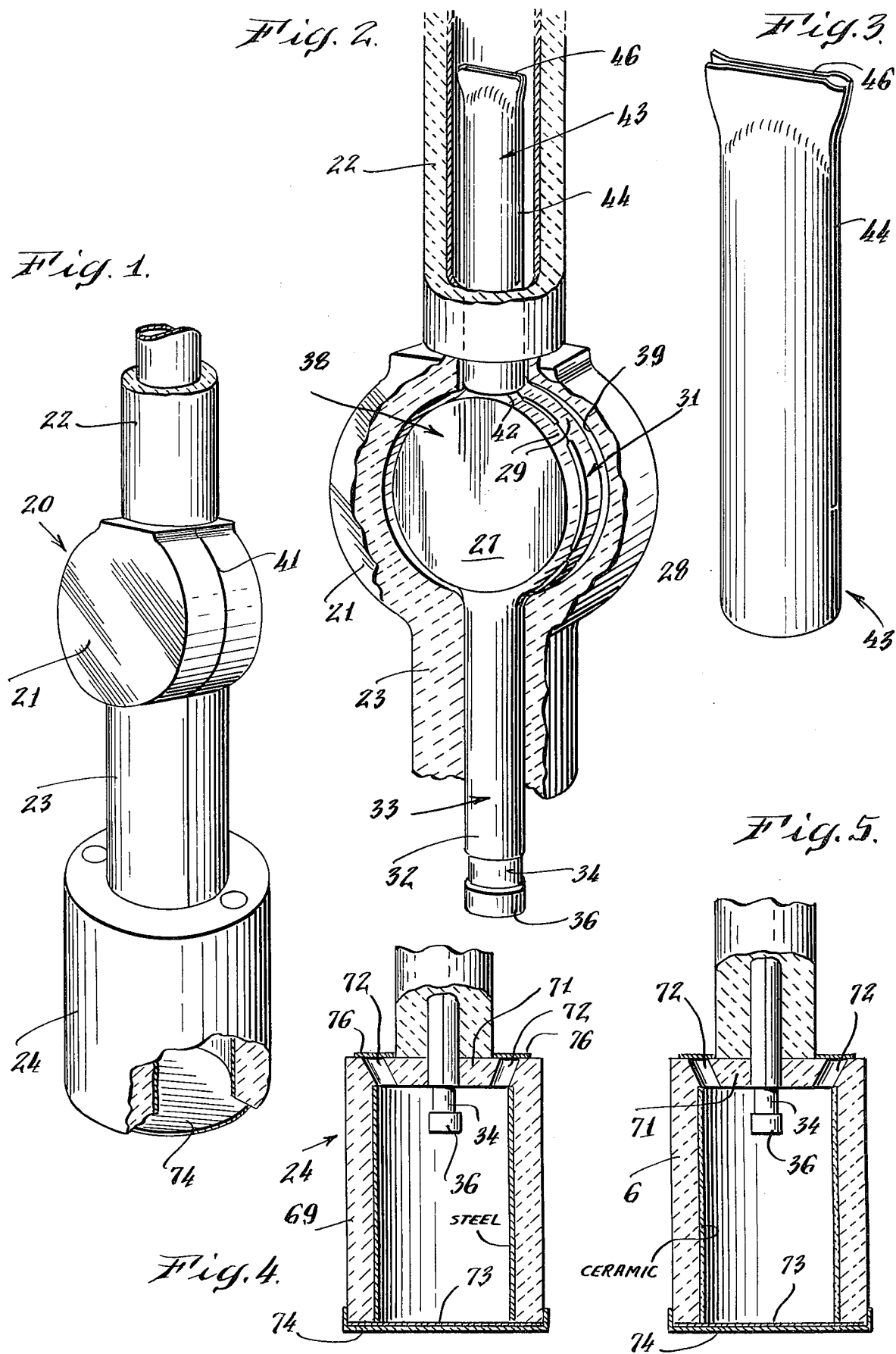

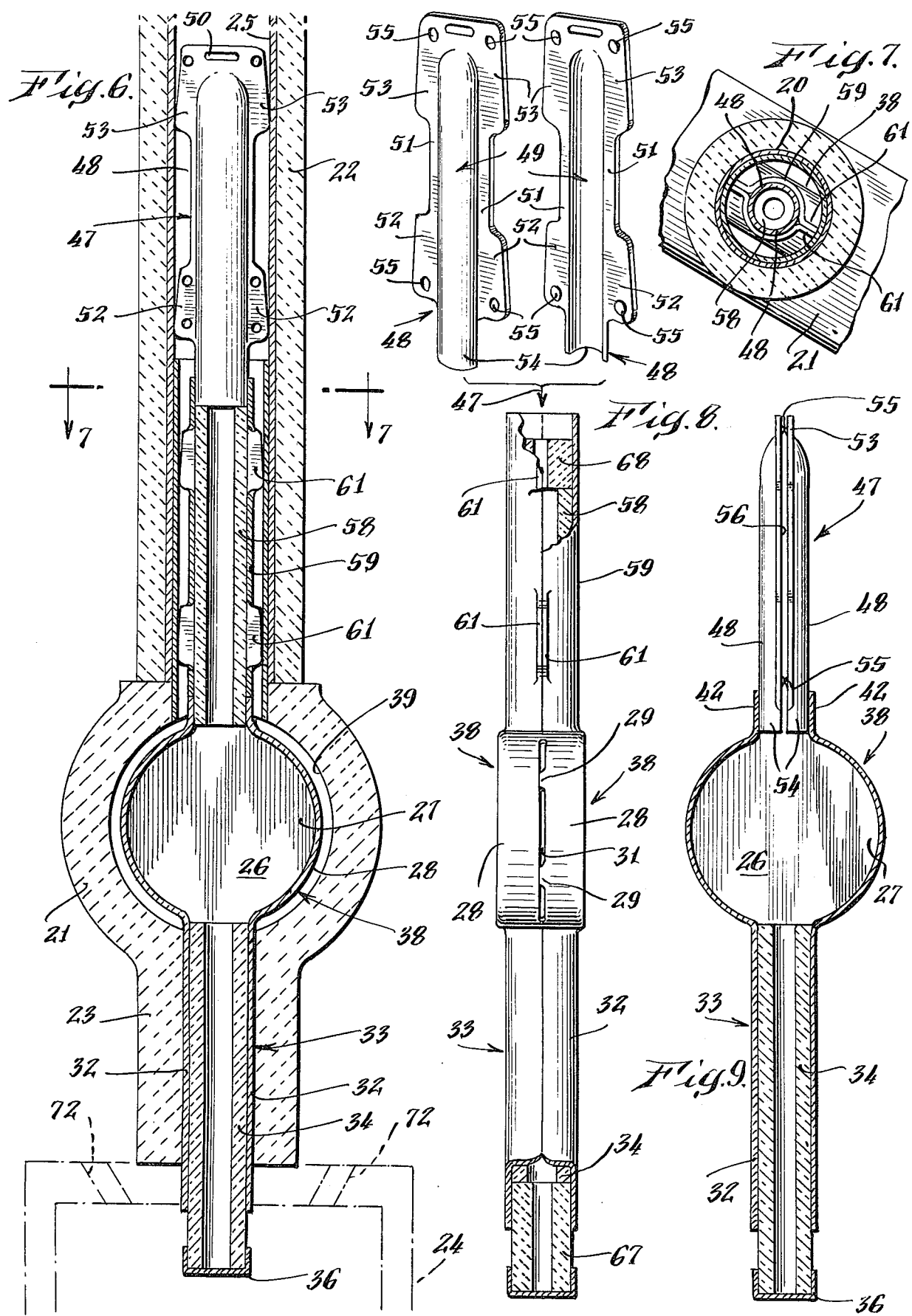

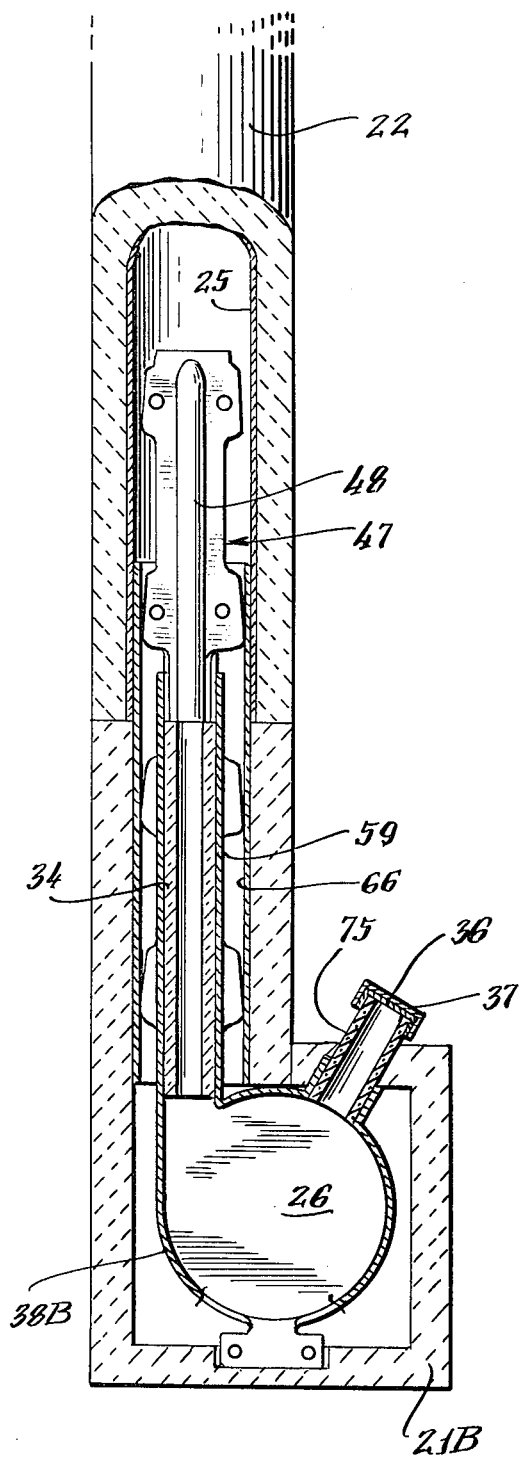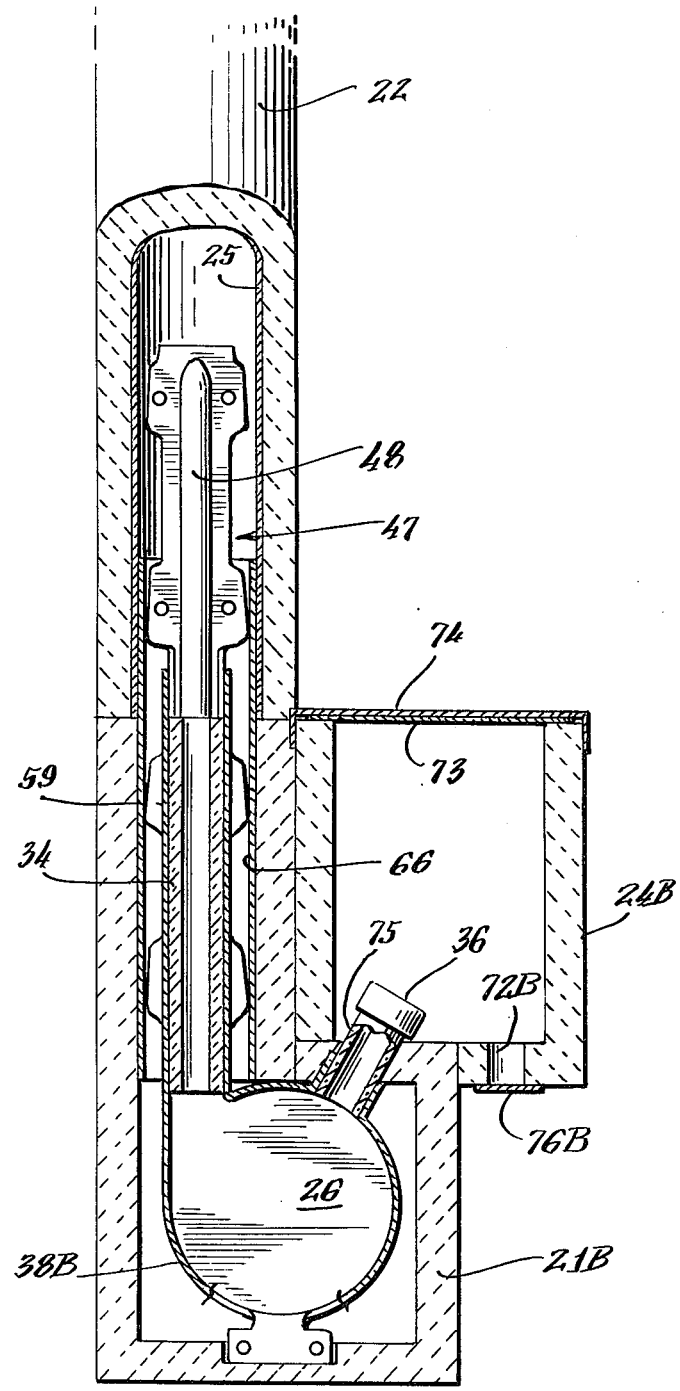

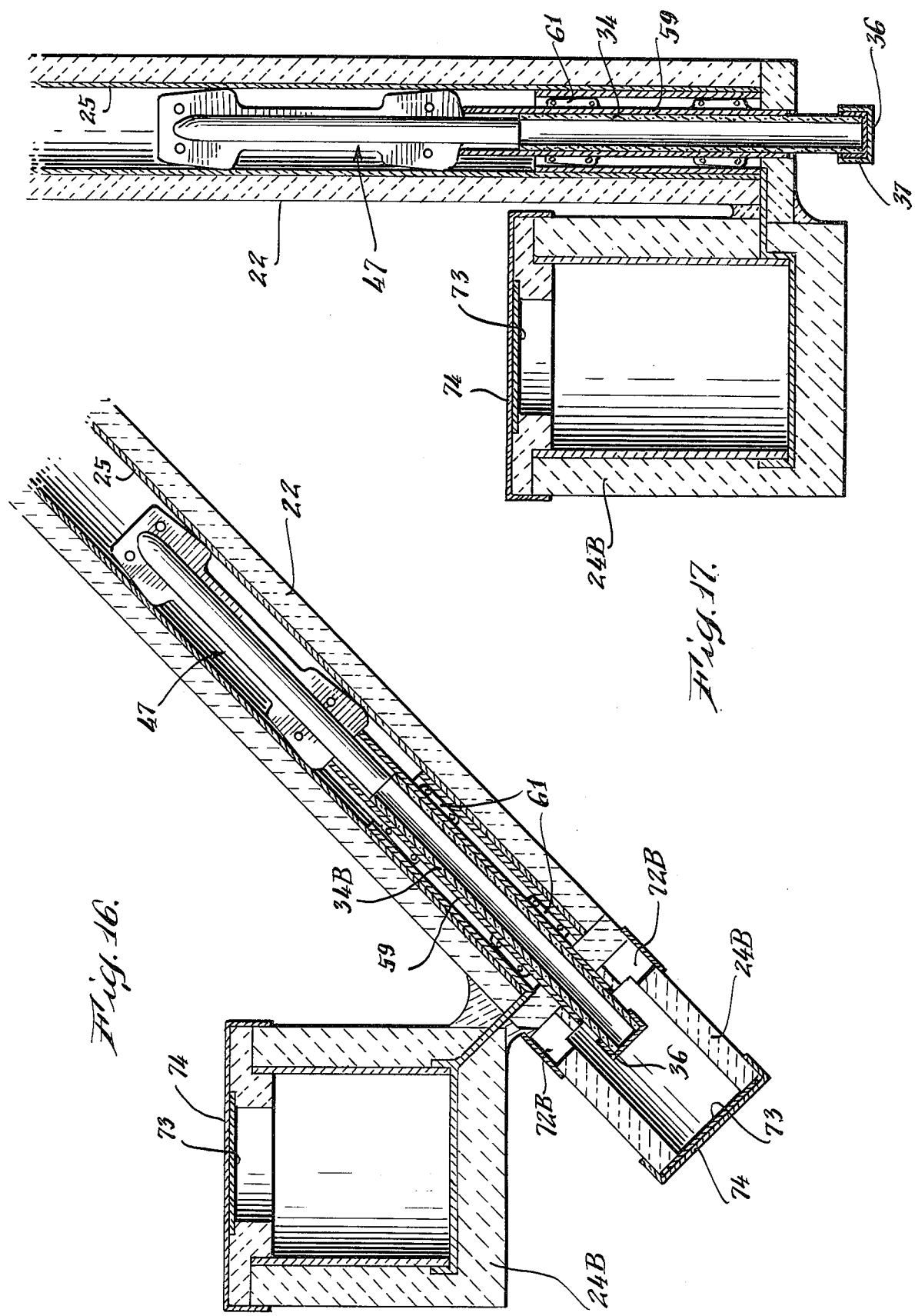

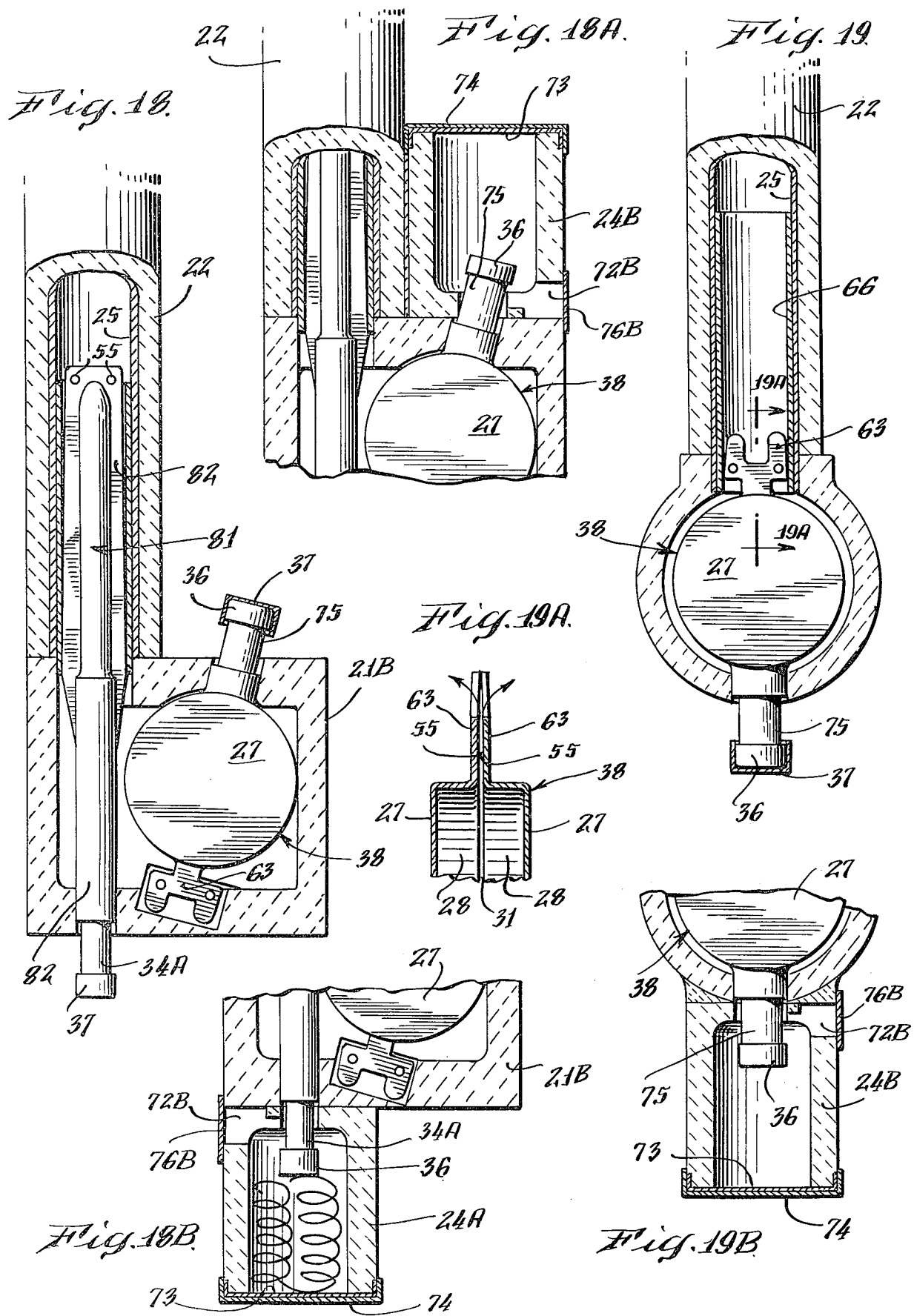

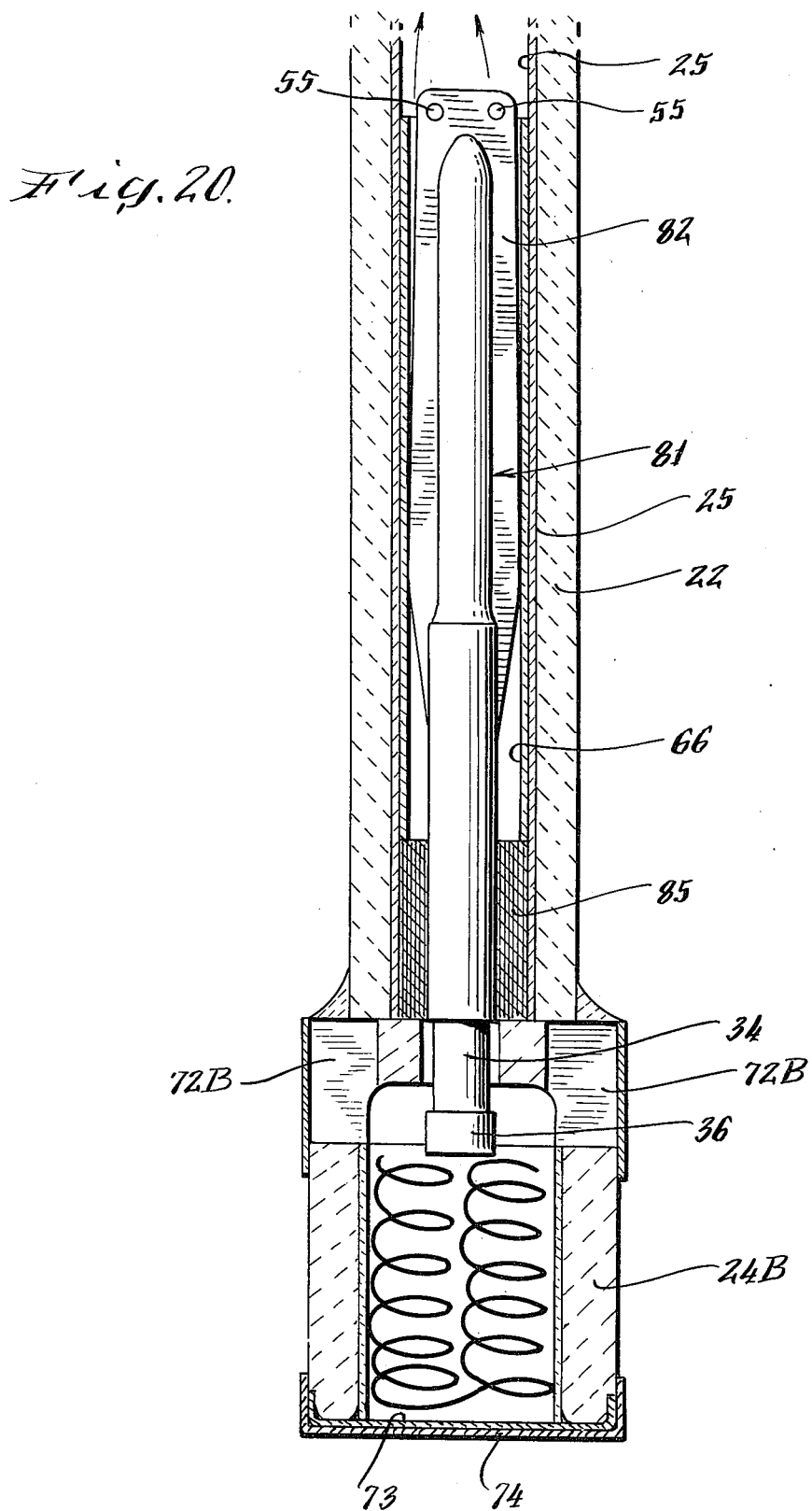

MOLTEN STEEL SAMPLERS

CROSS-REFERENCE TO RELATED APPLICATION

This is a continuation-in-part of my co-pending patent application 644,082 bearing the filing date of Dec. 24, 1975, and the present application supersedes that earlier co-pending application which is now abandoned.

This invention relates to sampling of molten metal to form pin samples and disc samples of the melt during its processing, for metallurgical analysis to permit precise corrections in its composition during the production of steel, alloys and like materials. In particular, this invention is concerned with the formation of disc and pin samples simultaneously in a single hollow sampler assembly, which is plunged through the overlying slag into a bath of molten metal to a depth of six or seven feet for example, and held in immersed position for the few seconds required to permit the inflowing melt to enter the sampler, displacing atmospheric air therefrom, after which the sampler is withdrawn from the melt. The solidified metal samples are quickly removed from the sampler and subjected to metallurgical analysis, allowing composition corrections to be made within minutes during the treatment of each heat of metal.

BACKGROUND OF THE INVENTION

My U.S. Pat. No. 3,561,494 describes a hollow steel-lined castable porous ceramic tube which has been widely adopted for supporting molten metal samplers during their immersion into the melt bath. For example, these samplers may take the forms shown in my U.S. Pat. Nos. 3,457,790, 3,452,602 or 3,686,949. The formation of pin samples and disc samples in glass-tube pin sample molds and in mating chill-block disc molds, which may be combined with glass-tube pin molds, in conjunction with closed, baffled or compartmented de-oxidizing chambers forms the subject matter of William J. Collins' U.S. Pat. Nos. 3,415,124, 3,415,125 and 3,656,350. The use of continuous vacuum sources for drawing molten metal into the chill mold is proposed in U.S. Pat. No. 2,515,060, and intermittent or plunger actuated vacuum samplers disclosed in U.S. Pat. No. 2,970,350 and 3,309,928. An evacuated sampler is disclosed in U.S. Pat. No. 3,357,250.

For various reasons, problems have been encountered with all of the types of samplers disclosed in these prior art patents. Vacuum samplers themselves are reasonably satisfactory, but the vacuum equipment necessary to obtain samples must be used in a dirty, hostile steel furnace environment, and the solidifying droplets or spattered molten metal and deposited layers of oxides, gums and moisture from the condensed hot gases of the melt clog and obstruct the vacuum passages of the vacuum system after a very few uses. This requires expensive baffle traps which must be disassembled after a very few sampling operations and cleaned in order to recondition the sampling assembly.

For these reasons, the prior art sampling devices of the kinds disclosed in these prior art patents have not met with complete acceptance and commercial success. An unfilled demand exists for a reliable sampler which will perform reproducible sampling operations and make dependable disc samples and pin samples, without bubbles or "pipe" inclusions of air or entrapped gasses in the sample itself, so that the sample may be quickly ground, polished, and subjected to metallurgical analysis without delay, and will provide a true representative sample of the molten metal under examination.

The use of two mating concave mold halves forming flat cylindrical pan-shaped chill molds, spaced apart by a slot of pre-determined width requires careful tolerances to release entrapped air sufficiently fast to permit a uniform sample to result when the sampler is used at particular depths or if the metal being sampled is at above-normal temperatures and thus more fluid and less viscous. When a combined pin-disc sample is desired, either the pin portion or the disc portion of the sample is likely to suffer from gas bubble inclusions, which interfere with the metallurgical analysis. U.S. Pat. No. 3,915,014 describes a sampler designed and manufactured by me, employed with a plastic entrance coating and a vacuum suction source, in order to collect satisfactory samples.

Prior standard sampling practice in obtaining samples in the steel industry for many years had been the use of spoons on long handles. The spoon is first "slagged", i.e., dipped into the hot slag at the surface of the melt. The hot slag freezes to the cold spoon, forming an insulating coating. The excess slag is poured off. The spoon is then dipped back into the furance deep enough to fill it with molten metal and then withdrawn. If the steel is "open" or unkilled, de-oxidant is added in wire form. Then the spoon contents are poured into mating halves of chill blocks. The procedure is: insulate, fill, kill and finally chill.

This has been proven to be the most accurate method of sampling over decades of steel making. "Immersion" samples allow for the extraction of samples at depths, or where conditions preclude the use of spoons, or where speed and time are important. The samplers described herein follow this procedure exactly; they insulate, fill, kill and chill in successive steps.

SUMMARY OF THE INVENTION

After building, testing and evaluating molten metal samplers for more than a decade, I have learned that vacuum suction systems are not required. I have discovered that the formation of uniform and homogeneous metal samples, avoiding the inclusion of trapped gases, requires the combined provision of air escape vents with entrance channels for the admission of the molten metal into the sampler while driving displaced air ahead of it at a steady measured pace. If insufficient provision is made for the release of entrapped air, as in the "permeable" sand mold body of U.S. Pat. No. 3,455,164, the inflowing sample is simply blocked by the trapped cushion of air and an unsatisfactory sample results.

The use of a riser vent tube of the kind shown in my U.S. Pat. No. 3,452,602 is helpful when only a pin sample is desired, as disclosed in that patent, but superior results are achieved with the slotted riser vent tubes of the present invention. As shown in the figures, these slotted riser vent components form a modification of the riser vent shown in my U.S. Pat. No. 3,452,602, with extended vent slots being formed down the sides to provide a restricted but substantial cross-sectional vent area.

The slotted riser vent assembly may be formed in two or more parts as concave plates, spaced apart by a gap of 0.001 inches to 0.020 inches around their entire periphery, and together forming a generally cylindrical tube telescoped over the air outlet or exit end of the sampler unit. In order to produce useful samples of unkilled steel incorporating substantial percentages of oxygen, a de-oxidant such as aluminum, magnesium or titanium may be provided in the form of an entrance cap spanning the entrance of an apertured de-oxidizing retort portal cemented to the inlet end of the sampler assembly. If desired, additional de-oxidant materials may be provided as wire or finely divided powder within the portal, which is temporarily closed during immersion by the inlet cap.

In order to be effective, such inlet portals must be provided with entrance and exit apertures allowing the inrushing molten metal to displace entrapped air while it is being de-oxidized, thus minimizing the volume of air driven through the sampler during the sampling operation. For this reason, a closed de-oxidizing chamber providing no exit for entrapped air as in U.S. Pat. No. 3,415,124 cannot produce adequate solidified samples of the melt.

Accordingly, a principal object of the present invention is to provide reliable and reproducible samples of molten steel taken from the melt during its melting and refining treatment, for metallurgical analysis and collection of the melt composition.

Another object of the invention is to provide methods and apparatus for the formation of such solidified samples of molten metal, affording elongated escape slots operating in conjunction with the slots in the chill mold halves for the release of entrapped air driven through the sampler ahead of the inflowing molten metal, which cannot be clogged or blocked by solidified, spattered particles of the melt and yet will release the entrapped air at a rate sufficiently great to avoid large or small bubbles or gas inclusions in the resulting sample.

A further object of the invention is to provide slotted riser vent assemblies for use with molten steel samplers, providing greatly elongated air escape vent slots through which entrapped air is discharged during the formation of the molten metal sample.

Still another object of the invention is to provide samplers of the above character and further incorporating apertured de-oxidizing retort portals, wherein the entering molten steel is de-oxidized before it forms the sample while at the same time air entrapped within the de-oxidizing portal is vented and diverted from entering the sampler and where molten in the de-oxidizing retort portal is drained therefrom upon withdrawal of the sampler of the molten steel in the furnace.

Other objects of the invention will in part be obvious and will in part appear hereinafter.

The invention accordingly comprises the features of construction, combinations of elements, and arrangements of parts which will be exemplified in the constructions hereinafter set forth, and the scope of the invention will be indicated in the claims.

For a fuller understanding of the nature and objects of the invention; reference should be had to the following detailed description taken in connection with the accompanying drawings, in which:

FIG. 1 is an external perspective view of a sampler of the present invention;

FIG. 2 is a partial cut-away perspective view of the upper portion of the sampler shown in FIG. 1;

FIG. 3 is a perspective view of a slotted riser vent tube incorporated in the embodiment of FIG. 2;

FIG. 4 is a fragmentary cross-sectional elevation view of the apertured de-oxidizing retort portal forming the lower portion of the embodiment of FIG. 1;

FIG. 5 is a similar fragmentary cross-sectional elevation view of a modified form of the apertured de-oxidizing retort portal shown in FIG. 4;

FIG. 6 is a cross-sectional front elevation view of a different embodiment of the invention capable of forming a disc sample combined with two pin samples in one unitary sample formed in a single sampling operation, and incorporating a different form of slotted riser vent tube.

FIG. 7 is a cross-sectional plan view taken along the plane 7—7 shown in FIG. 6, indicating the cooperating structure of the slotted riser vent tube and other sampler components there shown.

FIG. 8 is a cross-sectional side elevation view of a still different embodiment of the invention incorporating reduced diameter inlet and outlet sleeves further retarding the velocity of the inflowing molten metal and the outflowing displaced air expelled by the molten metal during the sampling operation and incorporating an exploded perspective view of the form of slotted riser vent tube shown in FIG. 6.

FIG. 9 is a cross-sectional front elevation view of still another embodiment of the invention incorporating a sampler forming a disc and single pin sample and showing a side elevation view of the slotted riser vent tube illustrated in FIG. 6.

Figure 12:
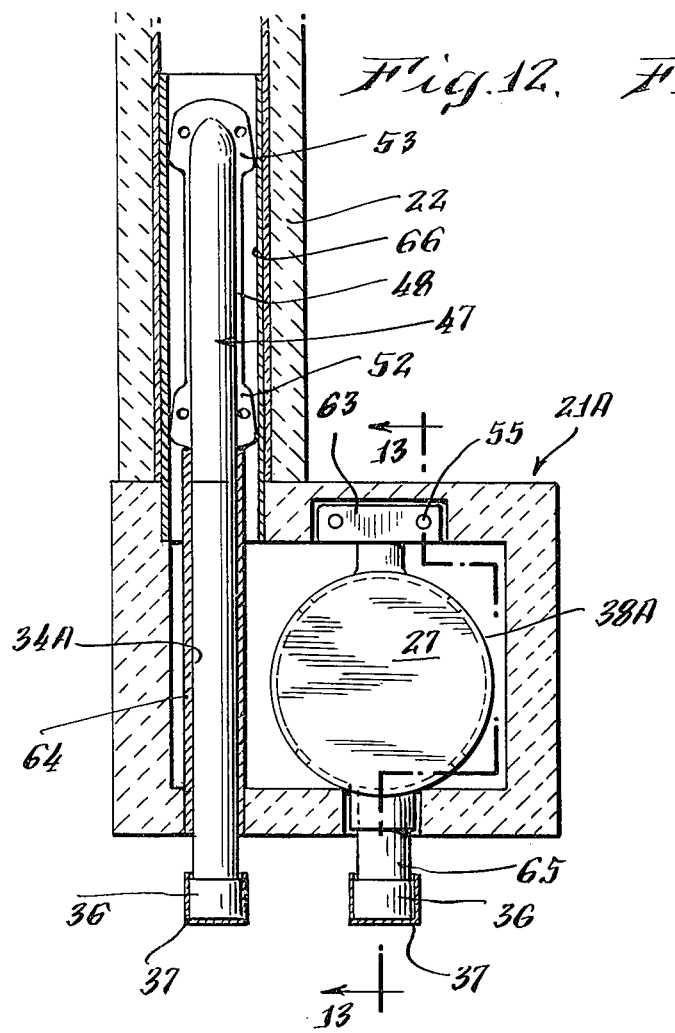
Figure 13:
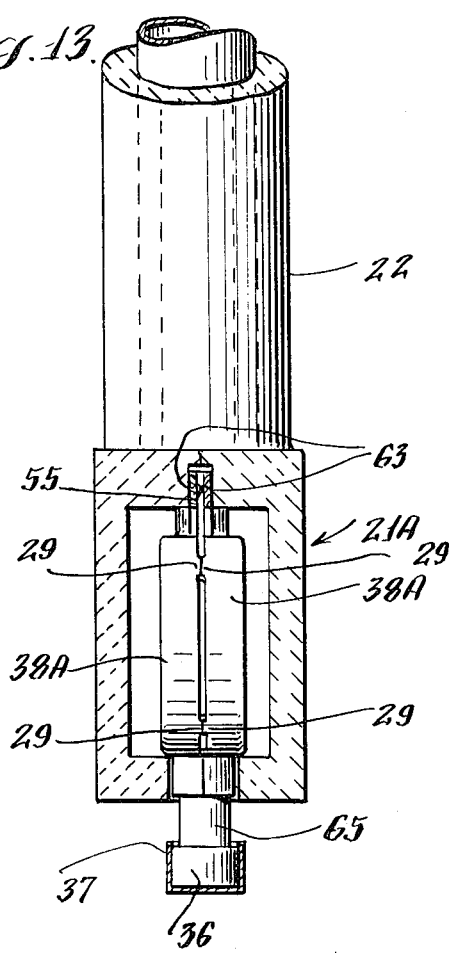
Figure 14:
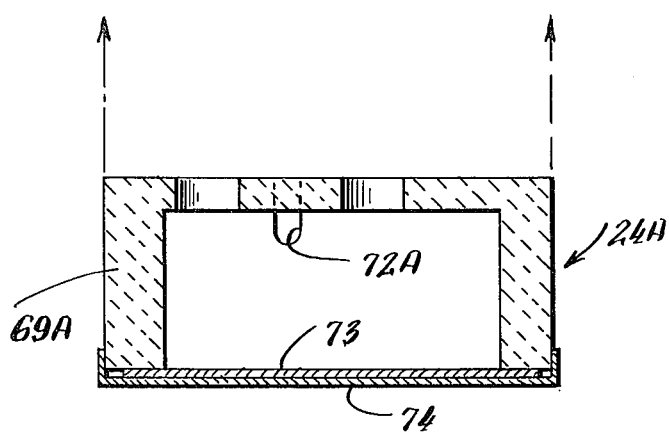
Figure 15:
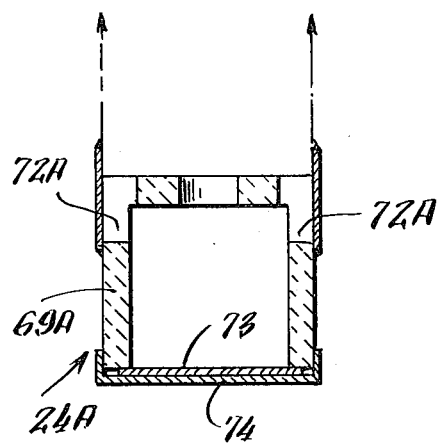

FIG. 10 is a cross-sectional front elevation of still another embodiment of the invention, incorporating a sampler forming a combined disc-pin sample vented by a slotted riser vent tube of the kind illustrated in FIGS. 6–9 with a short inlet entrance facing upward;

FIG. 11 is a cross-sectional front elevation view of a modified form of the embodiment shown in FIG. 10, further including an upward facing apertured de-oxidizing retort portal enclosing the upward facing inlet of the device;

FIG. 12 is a cross-sectional side elevation view of a still different embodiment of the present invention incorporating separate sampler molds for the formation of the disc sample and the pin sample enclosed in the same porous insulated ceramic housing cemented to the end of a steel-lined porous insulated ceramic immersion tube, with the pin sample mold being provided with a slotted riser vent tube of the kind shown in the previous Figures;

FIG. 13 is a cross-sectional side elevation view of the sampler shown in FIG. 12 taken along the broken plane 13—13 shown in FIG. 12;

FIG. 14 is a modified form of apertured de-oxidizing retort portal incorporating the air release vent and melt draining features of the portals shown in FIGS. 1, 4 and 5, and adapted to be incorporated in the sampler shown in FIG. 12;

FIG. 15 is a cross-sectional side elevational view of the apertured de-oxidizing retort portal shown in FIG. 14;

FIGS. 16 and 17 are cross-sectional side elevation views, showing two other embodiments of the invention incorporating the slotted riser vent tube and a pin sampler mold, all coaxially mounted at the lower end of a steel lined insulating porous ceramic immersion tube, each of which is also provided with a sampler bowl assembly similar to those shown in my U.S. pat. No. 3,686,949, for forming a large cylindrical block sample, with FIG. 16 also showing a de-oxidizing retort portal.

FIG. 18 is a cross-sectional side elevation view of still another embodiment of the invention showing a dual-purpose sampler housing enclosing a pin-sampler tube having a downwardly protruding entrance portal, and a disc sampler having an upwardly protruding entrance portal, each incorporating the slotted vent tube of the present invention.

FIG. 18A is a fragmentary sectional side elevation view of a modified form of the embodiment shown in FIG. 18 incorporating a de-oxidizing retort portal chamber enclosing the upwardly protruding entrance portal of the disc sampler, FIG. 18B is a fragmentary cross-sectional side elevation view of still another modified version of the embodiment of FIG. 18 showing a de-oxidizing retort portal chamber enclosing the downwardly protruding entrance portal of the pin sampler tube;

FIG. 19 is a cross-sectional side elevation view of still another embodiment of the invention showing a disc sampler with a downwardly protruding entrance portal enclosed in a sampler housing and having its slotted vent exposed inside the immersion tube for venting displaced air from the interior of the disc sampler through the immersion tube to the atmosphere in the same manner as the other embodiments of the invention.

FIG. 19A shows a fragmentary enlarged cross-sectional end elevation view of the disc sampler mold halves in FIG. 19, showing the slotted riser vent formed between these spaced apart sampler mold halves;

FIG. 19B is a fragmentary cross-sectional side elevation view of a modified embodiment of the invention shown in FIG. 19 incorporating a de-oxidizing retort portal chamber enclosing the downwardly protruding entrance portal of the disc sampler; and FIG. 20 is a cross-sectional side elevation view of a further embodiment of the invention incorporating a pin sampler with an enlongated slotted riser vent tube frictionally engaged within a spacer tube positioned inside the tubular metal liner of the immersion tube and incorporating a deoxidizing retort portal chamber surrounding the downwardly projecting entrance portal of the pin sampler tube.

For a fuller understanding of the nature and objects of the invention, reference should be had to the following detailed description taken in connection with the accompanying drawings. The same reference numbers refer to the same elements throughout the several views of the drawings.

GENERAL DESCRIPTION

In all embodiments of the present invention, a slotted riser vent tube is provided at the uppermost end of a hollow sampler mold, which may take the form of a cylindrical tubular pin sample mold formed of high-temperature quartz glass for example, or may be a two-part mating flat cylindrical mold capable of forming disc samples, or may be a combination of disc and pin mold components capable of forming a combined sample incorporating a disc with one or two pins. In all of these forms of samplers, the measured advance of the entering molten metal must be rapid enough to expel entrapped air fast enough to avoid solidification until the sampler mold is filled by the melt, but it must not be so rapid that the advancing molten metal bypasses bubbles of entrapped air, incorporating them as inclusions in the solidified sample.

The slotted riser vent tubes of this invention retard the expulsion of entrapped air only enough to cause smooth, uniform inflow of the molten steel, while releasing the air at a sufficiently rapid rate through the greatly elongated vent slots to assure that the inrushing molten metal will not bypass bubbles of air, and will flow smoothly and uniformly upward into the sample mold, driving the air ahead of itself through the vent slots until the mold is filled. In addition, the elongated vent slots provide ample vent area, even after partial clogging by solidified spattered molten steel.

FIG. 1 is an external view of a sampler assembly 20, incorporating a porous ceramic disc sampler housing 21 secured by cement or the like to the lower end of a steel lined porous insulated ceramic immersion tube 22, with a generally tubular porous ceramic insulated pin sampler housing 23 extending from the lower end of disc sampler housing 21, and with an apertured de-oxidizing retort portal 24 extending downward from the lower end of pin sampler housing 23. Being cemented together, the portal 24, the housing 23 and the housing 21 form a solid continuous extension of the porous ceramic insulated immersion tube 22. Since the use of insulated cardboard or paper layers is substantially avoided, the extreme buoyancy generated by the explosive vaporization of insulated paper sampler housings is not encountered with the samplers of the present invention, and their immersion to considerable depths of six or seven feet below the surface of molten steel in a furnace is achieved without difficulty by a single operator. The sampler mold components enclosed within the housings of FIG. 1 are shown more clearly in the broken-away view of FIG. 2.

The embodiment of the invention shown in FIG. 2 incorporates the disc sampler housing 21 cemented to the immersion tube 22 and the pin sampler housing 23 joined to the lower end of the disc sampler housing 21, but omits the retort portal 24 shown in FIGS. 1 and is useful when deoxidizing action is not required, for example when sampling killed steel melts. Two flat concave cylindrical mold halves 38 form the disc sampler, being juxtaposed with their concave cavities in facing relationship to form an internal disc shaped mold cavity 26, shown in FIG. 6.

Disc chill mold halves 38 are preferably formed with concave pan shapes as described in U.S. Pat. No. 3,915,014, with a flat circular sidewall 27, ending in a short perpendicular rim flange 28 whose outer edge directly faces the outer edge of the corresponding rim flange 28 of the opposite mold half 38. These terminal edges of the rim flanges 28 are preferably formed with small projections 29 extending a few thousandths of an inch beyond the terminal edge of the rim flange, to space it away from the facing terminal rim flange edge of the opposite chill mold half 38 as shown in FIG. 2.

If desired, these projections 29 may be formed at three, four or more points around the periphery of the rim flange 28 for abutting relationship with the corresponding opposite projections 29 on the opposite rim flange 28 of the facing mold half 38.

Alternatively, as shown in FIG. 8, projections 29 may be formed at two or more points on only one side of the periphery of rim flange 28, on the right side for example as the observer views the concave internal cavity of the mold half 38, so that when the mold halves are juxtaposed with their cavities facing, the projections on each abut the rim flange edge of the oppsote mold half. This is seen in the central portion of FIG. 8. By this means, a peripheral spacing vent slot 31, best seen in FIGS. 2 and 8, is formed around the major portion of the periphery of the disc mold sampler formed on the mold halves 38, creating an exit vent for the escape of air displaced by the entering molten metal.

Extending downward from the disc mold halves 38 in FIG. 2 are two facing concave semi-cylindrical half sleeves 32. The mating concave juxtaposition of mold halves 38 brings the half sleeves 32 into facing abutting engagement. Together the half sleeves 32 form a tubular pin-mold retainer enclosure 33 embracing a pin mold sampler tube 34 of fused silica or "quartz" glass having high thermal shock resistance. As shown in FIGS. 6 and 8, the pin mold sampler tube 34 extends inside the entire length of the half sleeves 32 from the lower edge of the disc mold cavity 26 formed between the disc mold halves 38 to protrude beyond the end of the half sleeves 32 downward where its lower end may be exposed to receive the molten metal to be sampled.

The exposed lower end of sampler tube 34 is preferably covered by a sheet metal cap 36, which allows the immersion sampler to be plunged to the desired sampling depth into the molten metal bath before cap 36 is melted by the heat of the bath to admit the molten metal to be sampled. If desired, a protective slag cover 37 of paper or similar material encloses cap 36, preventing the external encrustation of cap 36 by adhering layers of insulating slag. The protective paper cap serves two purposes. In burning off it volatilizes explosively, removing the encrusted slag. Also, by selecting paper of proper thickness, total burn-off time can be extended to provide control over sampling immersion depths.

As indicated in FIGS. 2 and 6, the combined mold halves 38-32 forming the combined disc-pin sampler mold are enclosed inside a protective porous insulated ceramic housing 21-23.

The disc sampler housing 21 loosely embraces the disc mold halves 38 with an air space 39 surrounding them through which displaced air passing through the peripheral vent slot 31 between the two mold half rim flanges 28 is delivered to the interior of the porous ceramic insulated immersion tube 22 for venting to the atmosphere. The pin sampler housing 23 forms a cylindrical enclosure more closely embracing the half sleeves 32 forming the lower pin mold retainer 33, as shown in FIG. 6. The disc sampler housing 21 and the pin sampler housing 23 are preferably formed together in two mating halves, which are cemented together along an equatorial junction line 41 as shown in FIG. 1.

Slotted Riser Vent Tube

Shown in FIGS. 2 and 3 is one form of a slotted riser vent tube characterizing the sampler assemblies of the present invention. Another embodiment of this slotted riser vent tube is illustrated in FIGS. 6 through 11, formed in two mating stamped halves, and each of these slotted riser vent tubes provides a vertical tubular riser, extending upward from the disc mold halves 38 forming the disc mold cavity 26, inside the porous ceramic insulated immersion tube 22. The upper portions of the disc mold halves 38 are formed with upstanding semi-circular projecting flanges 42, blending into the rim flanges 28 extending up both sides of the disc mold halves 38, to form an upper outlet from cavity 26.

Slotted riser vent tube 43 shown in FIGS. 2 and 3 is telescopingly engaged with the flanges 42, thus forming an upstanding vent pipe receiving the air displaced from the interior of disc mold cavity 26 and pin mold sampler tube 34 by the inflowing molten metal. Riser tube 43 is formed with elongated side slots 44 extending along a substantial portion of both sides, and the upper ends of slots 44 are connected by an end slot 46.

Slots 44 and 46 are between 0.005 and 0.025 inches, and preferably between 0.010 and 0.020 inches in width, providing a substantial air vent cross-sectional area having such great length that it cannot be significantly clogged by any normal accumulated residue of solidified spattered molten metal droplets and particles which might block a smaller vent. At the same time, the relatively narrow width of slots 44 and 46 retards the exit of displaced air sufficiently to avoid splashing and turbulence in the advancing molten metal without blocking the air displacement enough to force the metal to bypass bubbles of air to form inclusions in the solidified sample.

In the different version of the slotted riser vent tube 47 shown in FIGS. 6-20, a pair of mating, convexly stamped, flanged vent plates 48, best shown in FIGS. 6, 8 and 9, are each provided with a concave semi-cylindrical vent cavity 49. A side flange 51 extends radially outward along the side of cavity 49, terminating in a wider base flange 52 near the lower end of the vent plates 48 and in a top end flange 53 near the upper end of the vent plates 48. A spot weld 50 joins the top flanges 53, to form a unitary riser vent tube 47.

The maximum overall width of the base flange 52 and the top end flange 53 is selected to fit snugly within the internal diameter of the steel tube 25 forming the internal wall of the porous ceramic insulated immersion tube 22. By this means, the two mating vent plates 48 are urged toward each other throughout their length in closely juxtaposed facing relationship near a diametral plane of the immersion tube 22.

The vent plates 48 are preferably provided with indented dimples 55 formed in their base flanges 52 and their top end flanges 53, protruding toward each other in their juxtaposed relationship, assuring that they will be spaced apart by a predetermined distance, preferably between 0.010 inches and 0.020 inches, around their entire periphery.

The lower ends of each of the vent plates 48 form a short semi-cylindrical extension 54 preferably dimensioned for telescoping insertion between the upstanding flanges 42 on the disc mold halves 38. Being gripped between the upstanding semi-circular flanges 42, the downwardly extending semi-circular extensions 54 are positioned to hold the vent plates 48 in closely abutting facing engagement, spaced apart only by the predetermined width of vent slots 56 extending around their entire remaining periphery, whose width is measured by the height of the dimples 55 deformed in the base flanges 52 and top end flanges 53. The vent plates 48 are further secured by their telescoping insertion inside the bore of immersion tube 22, which is slipped downward over the vent plates into abutting engagement with the upper end of disc sampler housing 21, where the ceramic tube 22 and the ceramic housing 21 are cemented into firmly anchored relationship to form a modified version of the assembly illustrated in FIG. 2, with the two-part vent plates 48 forming the vent tube 47 in place of vent tube 43 there illustrated.

Both forms of the riser vent tubes 43 and 47 incorporate similar elongated peripheral slots extending up both sides and across their upper ends. Side slots 44 joined by end slot 46 provide this air vent slot in riser vent tube 43. The vent slots 56 extending up both sides and across the upper end of the assembly 47 of vent plates 48 form a substantially similar vent slot in the two-part riser vent tube assembly 47. Both of these slotted riser vent tubes thus provide the reduced velocity of displaced air required to cushion the inflow of the entering molten metal without blocking the air flow enough to prevent bypassing and inclusion of air bubbles.

Disc-and-Upstanding-Pin Samplers

In such prior art U.S. Pat. Nos. 3,656,350 and 3,915,014, combined disc-pin samples resembling a lollipop are shown, with a downwardly extending pin sample forming the lower part of the disc-pin assembly. Satisfactory pin-disc samples in this configuration can occasionally be secured in the samplers described in these prior art patents, but many unsatisfactory samples are normally secured as well, requiring half a dozen sampling operations to produce a single useful sample in many cases. It is believed that this lack of reproducibility and reliability is caused by inadequate venting afforded by the samplers described in these patents, in conjunction with temperature and sampling depth variations producing drastic viscosity changes. By contrast, the samplers of the present invention with their upstanding slotted riser vent tubes 43 or 47 provide unusually satisfactory venting operation, and reliable, reproducible samples are secured in nearly every sampling operation performed with the devices of the present invention.

Indeed, the cushioned and retarded advance of the molten metal into the sampling cavities of the samplers of this invention is so smooth and steady that uniform, nonporous, homogeneous samples incorporating both a pin and a disc of metallurgically uniform composition are so readily achieved that an additional pin sample segment of these compound samples can be produced simultaneously in the same sampling operation. This is achieved by the sampler assemblies illustrated in FIGS. 6 and 8, where an upper pin mold sampler tube 58 is installed, telescoped within the semicircular upstanding flanges 42 of the disc mold halves 38, protruding upwardly inside the steel-lined immersion tube 22 to terminate in a slotted riser vent tube 43 or 47 in the manner illustrated in FIG. 6.

If desired, a supplemental alignment tube 59 having laterally offset guide flanges 61 at its upper and lower ends may enclose the upper pin mold sampler tube 58. The alignment tube 59 is preferably formed of steel, while the upper pin mold sampler tube 58 is formed of a high-temperature quartz glass, zirconia, or similar smooth refractory material. Guide flanges 61 serve to center the sampler tube 58 substantially coaxially inside the immersion tube 22.

For ease of assembly, the lower pin mold sampler tube 34 and the upper pin mold sampler tube 58 are customarily cemented into the disc mold halves 38, the alignment tube 59 may be cemented in the same manner in its telescoped relationship embracing upper pin sampler mold tube 58, to secure the entire assembly of the disc mold halves and both pin sampler mold tubes in their cooperative relationship. The lower pin mold tube 34 thus has its central bore leading directly into the disc mold cavity 26, which communicates directly with the central bore of the upper pin sampler mold tube 58.

As shown in FIG. 6, the melting of cap 36 by the heat of the melt admits molten metal directly into the lower pin sampler mold tube 34. Molten metal rising within tube 34 forces ahead of it the displaced air, which passes upward through disc mold cavity 26 and upper pin mold tube 58. Part of this air escapes through the peripheral slot 31 (FIG. 8) between the rim flanges 28 of the disc mold halves 38, and the balance of this displaced air moves upward into the slotted riser vent tube 43 or 47 where it escapes through the elongated slots 44-46, or the corresponding slots 56 formed between the vent plates 48 as shown in FIG. 9.

"Parallel" Samplers

In the forms of the invention illustrated in FIGS. 12, 16, 17 and 18, separate sampler molds are filled with molten metal simultaneously during the plunging immersion of the sampler assembly beneath the slag layer into the bath of molten metal. In the sampler assembly shown in FIG. 12, a pair of disc mold halves 38A incorporating no half sleeves or upstanding semi-circular flanges are provided with a pair of alignment tabs 63 protruding upward from their upper rim edges. The tabs 63 are provided with a pair of dimples protruding in opposite directions, the left dimple being upset convexly toward the facing tab 63 and the right dimple being offset concavely away from the facing tab 63, permitting the face-to-face alignment of these tabs 63 to bring the protruding deformed dimples of each into interfitting socketed engagement in the corresponding dimple recess of the facing tab 63.

The mold halves 38A are also provided with rim projections 29 for face-to-face alignment, leaving a vent slot 31 extending around substantially the entire periphery of the resulting cavity 26, and opening into the interior of a disc sampler housing 21A socketed to receive the abutting tabs 63, and also provided with a downward facing entrance aperture chamfered to receive the lower end of the mold halves 38A and also accommodating a short entrance tube 65 cemented therein and provided with a metal cap 36 and a paper slag cover 37.

Tabs 63 are preferably spaced apart by their dimples or by slightly bent rims to maintain a vent slot 0.010 inches to 0.020 inches wide around their entire periphery, as indicated in FIGS. 13 and 19A.

The disc sampler housing 21A is large enough to accommodate the mold halves 38A, and also a pin sampler mold tube 34A positioned if desired in a protective steel cover tube 64 and extending through an entrance aperture in the lower portion of housing 21A to form a corresponding sampler entrance similar to that of entrance tube 63 and likewise provided with a steel cap 36 and a paper slag cover 37. Cover tube 64 extends upward through the upper exit aperture formed in the housing 21A beyond the upper end of pin sampler tube 34A into telescoping engagement with a slotted riser vent tube 47, formed by two vent plates 48 as shown in FIG. 8, whose base flanges 52 and top flanges 53 serve to position the pin sampler assembly centrally and coaxially within the supporting immersion tube 22 whose lower end is cemented to the upper portion of housing 21A around its exit aperture embracing cover tube 64.

Vent space is provided inside the exit aperture of housing 21A connecting its interior with the bore of immersion tube 22, utilizing an alignment tube 66 interposed between flanges 52 and 53 of vent plates 48 and the internal steel tube forming the inner wall of immersion tube 22. This vent space allows the air displaced through peripheral slot 31 between mold halves 38A to travel upward into the immersion tube 22, where it is joined by the air displaced from pin sampler tube 34A through the slots between vent plates 48, for venting to the atmosphere.

The pin sampler tube 34B incorporating a similar slotted riser vent tube 47 comprising vent plates 48 extending into the interior of immersion tube 22A is also shown in FIG. 16, where the immersion tube 22A also supports a large upward facing bowl-type sampler of the kind shown in my U.S. Pat. No. 3,686,949, and employed to collect large cylindrical blocks of solidified metal from the melt for metallurgical sampling purposes. Thus the samplers of FIGS. 12, 13, 16, 17 and 18 may be called "parallel" samplers since two separate samples are collected simultaneously during the immersion sampling operation.

In the modified embodiment illustrated in FIG. 8, a short length of quartz glass entrance tube 67 is connected to the entrance end of the lower pin mold sampler tube 34 directly abutting its lower end. Entrance tube 67 is provided with a smaller internal diameter than pin sampler mold 34, tending to retard the velocity of the entering molten metal moving upward within the pin mold sampler 34. A similar exit tube 68 also having a smaller internal diameter is mounted at the upper end of the upper pin mold tube 58 inside the alignment tube 59, tending to retard the exit velocity of the displaced air driven ahead of the rising molten metal expelled from the sampler assembly.

Either or both of these tubes 67 and 68 may be used if desired in other embodiments of the invention to reduce the speed of the sampling operation, to avoid spattering and swirling surface flow "Coanda" flow patterns which may tend to coat the mold surfaces with layers of solidified metal from the melt, entrapping large volumes of air as air bubble inclusions therein sometimes resembling a baked "pop-over". Velocity control and ample air venting provided in the samplers of the present invention both serve to eliminate these sources of sample discontinuities or gas-bubble inclusions, and uniform homogeneous solid metal samples are produced in each sampling operation performed with the samplers of this invention.

APERTURED DE-OXIDIZING RETORT PORTALS

The retort portal 24, shown at the lower end of the external perspective view of FIG. 1 and shown in cross-section in FIGS. 4 and 5, is typical of the apertured deoxidizing retort portals which may be employed if desired with the samplers of the present invention when de-oxidizing is required. As shown in the cross-sectional elevation view of FIG. 4, these retort portals are bounded by a sidewall portion 69 forming a substantially cylindrical casing whose upper end is spanned by a topwall portion 71 having one, two or more vents 72 formed therethrough, as well as a central aperture accommodating the protruding entrance end of a downwardly extending pin sampler mold tube 34 whose lower entrance end protrudes into the interior of the portal 24.

The portal of FIG. 4 is shown with a thin interior wall of steel having a thickness too small to provide any substantial chilling effect upon the molten metal entering the portal 24, contributing only a small part of the temperature reduction needed to solidify the sample. Spanning the lower open end of a portal 24 is a de-oxidant lid 73, also employed like cap 36 to retard the entrance of molten metal until the desired sampling depth has been achieved during the immersion of the sampler assembly. An outer slag cover 74 of paper or the like is employed to avoid accumulations of slag coatings on the thin sheet metal lid 73 and to provide a vaporizing explosive slag removal.

In the similar portal embodiment shown in FIG. 5 the interior of the concave portal cavity is lined only with a smooth ceramic coating rather than with a sheet metal wall, minimizing outgassing of the porous ceramic housing 24. In use, the plunging immersion of the sampler shown in FIGS. 1 and 4 through the slag layer into the molten metal results in the explosive vaporization of the paper slag cover 74 and the subsequent melting of the de-oxidizing sheet metal lid 73. The lid 73 is preferably formed of such de-oxidizing material as aluminum, magnesium or titanium, providing the desired de-oxidizing reaction with the unkilled molten steel entering the portal 24, which expels entrapped air through one or more vents 72 as it rises within portal 24. The vents 72 are preferably covered temporarily by slag covers such as the paper discs 76 in order to keep slag from coating and clogging the vents 72, and prompt vaporization of the paper slag covers 76 exposes these vents for the release of entrapped air at the sampling depth. When the de-oxidizing reaction is substantially completed, the molten metal within portal 24 melts the protective cap 36 and the de-oxidized melt immediately flows into the sampler assembly shown in FIG. 2. Cap 36 is formed of sheet metal between 0.020 and 0.050 inches thick, selected to provide the desired de-oxidizing time.

The optional portal 24 is shown in dashed lines in FIG. 6, where it is cemented to the lower end of the pin sampler housing 23, performing in the manner just described. A similar apertured de-oxidizing retort portal 24A is illustrated in FIGS. 14 and 15, with a top wall 71 apertured to receive both of the entrance tubes 63 and 36 in the parallel sampler shown in FIG. 12, and wherein the vents 72A are positioned in the sidewall 69A, providing the same air escape operation just described.

The portals of FIGS. 4 and 14 both readily permit draining of molten metal therefrom upon withdrawal of the sampler from the molten metal bath after filling of the sampler interior has occurred. This avoids any substantial solidification of metal within the de-oxidizing portal such as that occurring in the de-oxidizing chambers shown in Collins Pat. No. 3,415,125, for example, where a solid block of metal solidified in these chambers must be removed from the sample before metallurgical examination.

In the modified embodiments shown in FIGS. 10 and 11, the same slotted riser vent tube 47 is employed to vent air expelled from the upper pin mold sampler tube 34 in the manner described with reference to the samplers of FIGS. 2, 6, 12 and 16. The tube 34 extends upward from the disc mold halves 38B, which perform the same sample disc molding function previously described, and are loosely surrounded by disc sampler housing 21B. In this case, however, a short inlet tube 75 faces upward for top filling of the sampler, while the expulsion of air ahead of the molten metal sample occurs as already described. An apertured de-oxidizing retort portal 24B having a downward facing vent 72B and an upward facing open entrance surrounds the inlet tube 75 in the modified embodiment of FIG. 11, providing the same deoxidizing action described with reference to the de-oxidizing retort portals of FIGS. 4 and 14, and allowing the same self-draining operation upon withdrawal of the sampler from the melt.

Still another "parallel sampler" embodiment of the invention is shown in FIG. 18. Here the pin sampler tube 34A of refractory quartz glass is cemented inside a mating pair of riser vent plates 81 extending upward inside the sampler housing 21B. The upper ends of the mating vent plates 81 are stamped into lateral flanges 82, similar to flanges 52 and 53 in FIGS. 6 through 12, and likewise spaced apart by dimples 55 to assure a vent slot between 0.010 inches and 0.020 inches wide around the entire periphery of flanges 82.

As in the parallel sampler device of FIG. 12, the slotted vent riser tube 81-82 inside immersion tube 22 vents both the pin sampler mold 34A and the upward-facing disc sampler 38 enclosed in the same housing 21B.

An optional apertured de-oxidizing retort portal 24B may be cemented in place enclosing the upward-facing entrance 75 of disc sampler 38, as shown in FIG. 18A. A similar apertured de-oxidizing retort portal 24A may be cemented in place enclosing the downward-facing entrance of pin sampler 34A, as shown in FIG. 18B. Both of these retort portals are provided with drain vents 72B sealed by paper covers 76B, and with protective paper slag covers 74 enclosing metal caps 73. During immersion of the device in the melt, the explosive vaporization of paper cap 74 avoids accumulation of frozen slag, and the melting delay of metal cap 73 blocks the retort portal entrance until sampling depth is reached in the melt.

Metal cap 36 on the entrance to the sampler mold itself affords a similar time delay, assuring that inrushing molten metal will melt and mix with the de-oxidant material in the retort portal before entering the sampler mold.

The sampler entrances which are not enclosed in retort portals are provided with corresponding slag covers 37 enclosing metal caps 36 performing the same time delay and anti-slagging functions, assuring uncontaminated samples collected at the desired sampling depth.

When the sample has been collected, drain vents 76B permit air and molten metal to escape from the retort portal chamber under the influence of gravity during withdrawal from the melt, avoiding solidified blocks of metal in the portal chamber.

The embodiment of FIG. 19 combines the disc sampler 38 directly with the immersion tube 22. Spaced-apart vent tabs 63, with a vent slot between 0.003 inches and 0.010 inches wide around their entire periphery, are wedged into the lower end of an alignment tube 66 inside liner tube 25 in immersion tube 22, and the vent slot between tabs 63 vents the interior of disc sampler mold 38 directly into immersion tube 22 at the desired venting rate, as indicated in FIG. 19A.

For shallow sampling of molten metal, in cast iron production for example, or at eight to twelve inch depths as in "torpedo cars" carrying steel from blast furnace to steel mill, the immersion tube 22 is exposed to high melt temperatures for very brief periods. In such cases, immersion tube 22 may be formed of convolutely wound layers of paper as shown in FIG. 16 of my U.S. Pat. No. 3,686,949, for example. Such paper immersion tubes provide satisfactory performance with significant cost savings for such quick sampling immersions.

Even shallower sampling at four-inch or six-inch depths, as in continuous steel-ingot casters, for example, produces relatively low pressure differentials. In these cases, the comparatively small cross-sectional area of the vent slots between tabs 63, shown in FIGS. 12, 13, 18, 19 and 19A, together with the peripheral slots 31, provide ample venting of the disc samplers 38 in the embodiments shown in FIGS. 12, 13, 18 and 19.

If desired, a de-oxidizing retort portal may be cemented in place enclosing the downwardly facing entrance 75 of disc sampler 38 as shown in FIG. 19B.

A similar de-oxidizing retort portal 24B is shown in FIG. 20, enclosing the downwardly facing entrance of a pin sampler 34. The sampler 34, formed of a quartz glass tube, is cemented within mating vent plates 81 having vent flanges 82 spaced apart by dimples 55 to provide the desired vent slot spacing around the entire periphery of flanges 82. An alignment tube 66 is wedged between liner tube 25 of immersion tube 22 and the flanges 82. An annular, convolutely-wound paper core spacer 85 centers the pin sampler 34 at the lower end of immersion tube 22.

A pair of drain vents 72B permit the escape of air and molten metal during withdrawal of the sampler from the melt, as already described.

The apertured de-oxidizing retort portals of this invention thus provide successful de-oxidizing coupled with venting of air displaced from the portal, before sampling occurs. They are self-draining, and carry no excess metal from the melt when withdrawn. The resulting minimum weight of the filled sampler allows diagonal, slanting immersion and withdrawal without danger of breaking off an overloaded sampler, and the slotted riser vent tubes of the invention are fully operative at such slanting diagonal sampling angles, making the samplers of this invention useful in basic oxygen furances, ladles, tun dishes and electric furnaces.

The de-oxidizing reaction is exothermic, sometimes raising the melt temperature by 10° F, for example. The samplers of this invention thus delay chilling of the sampled metal until it has substantially filled the hollow sampler, employing the slight back pressure of the retarded displaced air vented through the slotted riser vent tubes to suppress spattering and turbulence rather than the premature chilling prior to or during de-oxidization produced by prior art immersion samplers.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A hollow, heat-insulated sampler for deep immersion in molten metal comprising:
   A. a hollow chill mold having an open entrance end for exposure to the molten metal,
   B. a protective cap temporarily closing the open entrance end during deep immersion movement of the sampler into the molten metal,
   C. a hollow, porous, heat-insulating ceramic housing enclosing the chill mold anchored to an elongated hollow heat-insulating support tube connecting the hollow interior of the housing to the atmosphere, and
   D. a slotted riser vent tube connecting the hollow interior of the chill mold to the interior of the support tube and having elongated vent slot means exposed to the support tube's interior, directing escaping air displaced from the hollow chill mold for venting to the atmosphere.

2. The sampler defined in claim 1, wherein the slotted riser vent tube is provided with vent slot means extending along its sides and across its distal end remote from the chill mold.

3. The sampler defined in claim 1, wherein the chill mold is formed of tubular high-temperature refractory material to form a pin sample.

4. The sampler defined in claim 1, wherein the chill mold is formed of two flat, cylindrical pan-shaped concave mold halves, facing each other to form a flat disc sample, with abutting rim flanges spaced from each other by a predetermined distance forming a vent slot around a major part of the periphery of the disc sample.

5. The sampler defined in claim 4, further including at least one pin sampler chill mold of tubular high-temperature refractory material communicating through the slotted vent riser tube with the hollow interior of the support tube.

6. The sampler defined in claim 5, wherein the disc sample chill mold is interposed in communicating relationship between a first entrance pin sampler tube and a second exit pin sampler tube.

7. The sampler defined in claim 5, wherein a single tubular pin sampler is interposed in communicating relationship between the disc sampler and the slotted vent riser tube.

8. The sampler defined in claim 1, wherein the slotted vent riser tube is formed of a plurality of stamped sheet metal plates, each having a central partial cylindrical recess and a peripheral edge, all juxtaposed with their central recesses forming a tubular central cavity and with their peripheral edges spaced apart to define vent slots extending along the sides and across the distal end of the vent riser tube.

9. The sampler defined in claim 1, further including a porous heat-insulating ceramic portal surrounding the open entrance end which is temporarily closed by the protective cap, and having vent means adjacent to the entrance end which is temporarily closed by slag cover means, and an enlarged open entrance opposite the vent means which is temporarily closed by a fusible de-oxidant lid.

10. A hollow, heat-insulated sampler for immersion in molten metal comprising a hollow sampler chill mold having an entrance end temporarily closed by a metal cap, and a porous heat-insulating concave ceramic portal surrounding the open entrance end temporarily closed by the metal cap, and having vent means adjacent to the entrance end and temporarily closed by slag cover means, and an enlarged open entrance opposite the vent means which is temporarily closed by a fusible de-oxidant lid.

11. The portal sampler defined in claim 10, wherein the open entrance is positioned to face downward as the sampler is immersed in the molten metal.

12. The portal sampler defined in claim 10, wherein the open entrance is positioned to face upward as the sampler is immersed in the molten metal.

13. The portal sampler defined in claim 10, wherein the portal encloses two entrance ends of two separate hollow sampler chill molds.

14. The portal sampler defined in claim 10, wherein the concave portal is lined by a thin metal lining over the major portion of its interior.

15. A hollow, heat-insulated sampler for immersion in molten metal comprising a hollow sampler chill mold having an entrance end temporarily closed by a protective cap, and a porous heat-insulating concave ceramic portal surrounding the open entrance end temporarily closed by the protective cap, and having vent means adjacent to the entrance end and temporarily closed by slag cover means, and an enlarged open entrance opposite the vent means which is temporarily closed by a protective entrance lid, enclosing fusible de-oxidant material within the concave portal.

* * * * *